US00PP09502P

United States Patent [19]

Challet

[11] Patent Number: Plant 9,502

[45] Date of Patent: Apr. 9, 1996

[54] CHRYSANTHEMUM PLANT NAMED 'CHALURIDO'

[75] Inventor: Jean-Pierre Challet, Lafayette, Calif.

[73] Assignee: Selection New Plant Sarl, Le Cannet des Maures, France

[21] Appl. No.: 273,999

[22] Filed: Jul. 12, 1994

[51] Int. Cl.[6] ..... A01H 5/00

[52] U.S. Cl. ..... Plt./76

[58] Field of Search ..... Plt./74.1, 76, 81, Plt./82

[56] References Cited

U.S. PATENT DOCUMENTS

| | | | |
|---|---|---|---|
| P.P. 2,119 | 1/1962 | Lamborot | Plt./76 |
| P.P. 3,890 | 5/1976 | Jessel, Jr. et al. | Plt./76 |
| P.P. 8,898 | 9/1994 | Glicenstein | Plt./76 |
| 4,616,099 | 10/1986 | Sparkes | 47/58 |

OTHER PUBLICATIONS

Broertjes, et al., 1980, "A mutant of a mutant of a . . . Irradiation of progressive radiation–induced mutations in a mutation breeding programme with *Chrysanthemum morifolium*", Euphytica, 29:525–530.

Gosling, ed., 1979, "The Chrysanthemum Manual—6th edition", The National Chrysanthemum Society, London, Essex Telegraph Press, LTD, pp. 329–336.

Broertjes, et al., 1978, "Application of Mutation Breeding Methods In the Improvement of Vegetatively Propagated Crops", Elsevier Sci. Pub. Co., New York, pp. 162–175.

Chan, 1966, "Chrysanthemum and rose mutations induced by X–rays", Am. Soc. Hort. Sci. Proc., pp. 613–620.

Broertjes, 1966, "Mutation breeding of chrysanthemums", Euphytica, 15:156–162.

Dowrick, et al., 1966, "The induction of mutations in chrysanthemum using X– and gamma radiation", Euphytica, 15:204–210.

Glazurina, et al., 1977, "Use of the method of artificial mutagenesis in the breeding of flower crops", Cytology and Genetics, vol. 11(3):237–240.

*Primary Examiner*—Howard J. Locker

*Attorney, Agent, or Firm*—Burns, Doane, Swecker & Mathis

[57] ABSTRACT

A new and distinct Chrysanthemum cultivar named 'Chalurido' is provided. The new cultivar is a mutation of the 'Chalecat' cultivar (U.S. Plant patent application Ser. No. 08/273,998, filed Jul. 12, 1994). Attractive large double incurved blossoms of the pompon type are formed that are Venetian violet on the inner ray floret surfaces and silvery lavender on the outer ray floret surfaces. The blossoms are long lasting and commonly keep their form for approximately three weeks on the plant and more than four weeks in a vase. The response period of the flowers is approximately nine weeks. Recurrent profuse flower production throughout the year is possible. The plant possesses strong thin stems, forms dark green glossy leaves, and commonly assumes a height of approximately 45 to 50 cm. The new cultivar is particularly suited for use in the production of a decorative pot Chrysanthemum that grows well single stem or disbudded. No growth regulator is necessary to achieve the short to medium plant height.

1 Drawing Sheet

SUMMARY OF THE INVENTION

The present invention comprises a new and distinct cultivar of Chrysanthemum, botanically known as *Dendranthema grandiflora,* and hereinafter is referred to by the cultivar name 'Chalurido'.

The new cultivar of the present invention was created through the gamma irradiation of the 'Chalecat' cultivar (U.S. Plant patent application Ser. No. 08/273,998, filed Jul. 12, 1994). The parent 'Chalecat' cultivar was formed by the crossing of the 'Siky' cultivar (non-patented in the United States) and the 'Prouesse' cultivar (non-patented in the United States) as described in my copending U.S. Plant patent application.

During June 1980, at Saint Paul Lez Durance, France, groups of 1,000 rooted cuttings of the 'Chalecat' cultivar having an age of two weeks were irradiated with gamma rays through the packing boxes at rates of 1.8, 2.5 and 3.0 Krads. Following irradiation the plants were shipped to Nuaille, Trementines, France, and planted in 4 liter pots, pinched, and grown outside until September, next grown in greenhouses, were not disbudded, and were carefully observed. It was found that most of the plants irradiated at a rate of 3.0 Krads died. Those plants that were irradiated at a rate of 2.5 Krads exhibited no growth following pinching and were discarded. Many different mutations were observed in the plants that were irradiated at a rate of 1.8

Krads. A single mutation that exhibits the characteristics of the 'Chalurido' cultivar was discovered among these plants. Also, a single mutation that exhibits the characteristics of the 'Chahalu' cultivar, (U.S. Plant patent application Ser. No. 08/273,996, filed Jul. 12, 1994) and a single mutation of the 'Chatupa' cultivar (U.S. Plant patent application Ser. No. 08/273,997, filed Jul. 12, 1994) were discovered among the same group of plants. It would have been impossible for a plant scientist to have predicted in advance that new cultivars having the combination of characteristics of the presently claimed 'Chalurido' cultivar and the sister 'Chahalu' and 'Chatupa' cultivars could have been formed even if the parent 'Chalecat' cultivar would have been available for such experimentation.

It was found that the new cultivar of the present invention:

(a) exhibits attractive large double incurved pompon blossoms that are Venetian violet on the inner ray floret surfaces and slivery lavender on the outer ray floret surfaces, (b) exhibits a flower response period of approximately nine weeks, (c) forms attractive dark green glossy foliage, (d) achieves a short to medium plant height, and (e) is particularly suited for pot mum production on a recurrent basis throughout the year.

The new cultivar is intended primarily as a decorative pot Chrysanthemum for growing indoors. However, it also can be grown for cut flower production in those instances where stems of approximately 40 cm. are acceptable. Also, the new cultivar can be grown outdoors at temperatures above freezing.

The new cultivar is particularly suited for single stem or disbudded growth. An increased number of branches readily can be induced by pinching. The pinching of a cutting commonly produces approximately 3 to 4 stems per cutting. No growth regulator is required to produce the short to medium plant height; however, a growth regulator optionally can be utilized.

The new cultivar can be considered to be an October-flowering greenhouse variety with the natural flowering season commonly occurring in weeks 42 and 43 of the year. Attractive blossoms can be produced on a recurrent bais throughout the year with the indicated nine week response period. The blossoms are long lasting and commonly can be maintained on the plant for approximately three weeks, and commonly exhibit a vase life of more than four weeks.

Asexual reproduction of the new cultivar by cuttings initially taken during 1981, as performed in Nuaille, Trementines, France, in a controlled environment has demonstrated that the characteristics of the new cultivar as herein described are firmly fixed and are retained through successive generations of asexual propagation.

'Chalurido' has not been observed under all possible environmental conditions to date. Accordingly, it is possible that the phenotype may vary somewhat with variations in the environment, such as temperature, light, day length, contact with pesticides and/or subjection to growth retardant treatments.

The 'Chalurido' cultivar of the present invention exhibits a combination of characteristics that readily distinguish it from the parent 'Chalecat' cultivar. For instance, the 'Chalurido' cultivar exhibits blossoms having Venetian violet on the inner ray floret surfaces and silvery lavender on the outer ray floret surfaces unlike the 'Chalecat' cultivar, the 'Chalurido' cultivar generally exhibits a smaller capitulum than the 'Chalecat' cultivar, an angular stem cross section unlike the round cross section of the 'Chalecat' cultivar, a stem coloration of Yellow-Green Group 144A unlike the stem coloration of Yellow-Green Group 146B of the 'Chalecat' cultivar, a more variable fine to coarse leaf serration unlike the medium to fine serration of the 'Chalecat' cultivar, approximately 37 to 40 leaves per typical stem in a long day crop before the bud opens unlike the lesser number of approximately 29 to 32 for the 'Chalecat' cultivar, a generally asymmetric leaf base unlike the 'Chalecat' cultivar, and a mucronate leaf apex unlike the acuminate leaf apex of the 'Chalecat' cultivar.

As indicated, other mutations of the 'Chalecat' cultivar are the 'Chahalu' cultivar and the 'Chatupa' cultivar. Each of these additional cultivars can be readily distinguished from the parent 'Chalecat' cultivar and from each other with respect to a number of plant characteristics.

The 'Chahalu' cultivar exhibits a lemon yellow capitulum unlike the 'Chalurido' cultivar, commonly forms a generally larger capitulum than the 'Chalurido' cultivar, a foliage coloration between Green Group 137A and 139A unlike the coloration Yellow-Green Group 147A of the 'Chalurido' cultivar, course leaf serration unlike the fine to course leaf serration of the 'Chalurido' cultivar, an acute leaf base shape unlike the asymmetric base of the 'Chalurido' cultivar, a cuspidate leaf apex unlike the mucronate leaf apex of the 'Chalurido' cultivar, and a diverging margin of sinus between lateral leaf lobes unlike the variably converging margin of the 'Chalurido' cultivar.

The 'Chalurido' cultivar exhibits a capitulum having inner surfaces of Venetian violet and silvery lavender outer surfaces unlike the 'Chatupa' cultivar, commonly forms a fully opened capitulum having a generally smaller diameter than the 'Chatupa' cultivar, a foliage coloration of Yellow-Green Group 147A unlike the foliage coloration of Green Group 137A for the 'Chatupa' cultivar, a more variable fine to coarse leaf serration than the medium serration of the 'Chatupa' cultivar, approximately 37 to 40 leaves per typical stem in a long day crop before the bud opens unlike the lesser number of approximately 29 to 32 for the 'Chatupa' cultivar, a variable converging margin of sinus between lateral lobes unlike the converging margin of the 'Chatupa' cultivar, a mucronate leaf apex unlike the cuspidate leaf apex of the 'Chatupa' cultivar, and a generally asymmetric leaf base unlike the rounded tending to cordate base of the 'Chatupa' cultivar.

The new 'Chalurido' cultivar is being marketed under the Violet Cymbal trademark.

BRIEF DESCRIPTION OF THE PHOTOGRAPH

The accompanying photograph of FIG. 1 was prepared during August, 1995, and shows as nearly true as it is reasonably possible to make the same in a color illustration of this character, typical plant parts of the new cultivar of the present invention. The plant was approximately 10 weeks of age and was grown at Half Moon Bay, Calif., U.S.A., under standard greenhouse conditions which approximate those commonly utilized for the production of decorative pot mums wherein three cuttings were placed in a single pot. The plant had been disbudded in order to encourage the formation of one large bloom per stem. There had been no application of a growth regulant. At the left are shown typical buds in various stages of maturity. At the center is shown a stem with typical foliage wherein the upper and under surfaces of the leaves are visible. At the top are placed three typical blossoms in various stages of opening that were obtained from other stems. At the right are shown typical leaves of various sizes.

DETAILED DESCRIPTION

The chart used in the identification of colors described hereafter is the R.H.S. Colour Chart of The Royal Horticultural Society, London, England. In some instances more common color terms are provided and are to be accorded their usual dictionary significance. The plants described were 10 weeks of age and were grown at Nuaille, Trementines, France, under standard greenhouse conditions which approximate those commonly utilized for the production of decorative pot mums.

Classification:

*Botanical.*—*Dendranthema grandiflora,* cv. 'Chalurido'.

*Commerical.*—Decorative pot mum.

Inflorescence

A. Capitulum:

*Form.*—Large, double, and incurved.

*Type.*—Pompon.

*Diameter across face.*—Approximately 12 to 14 cm. on average when fully expanded.

*Frequency.*—Corymbiform, and blossoms form in profusion (as illustrated). Night temperatures above 23° C. will delay flowering. Night temperatures as low as 14° C. generally can be tolerated, and even night temperatures as low as 5° to 10° C. can be tolerated during the bud opening stage.

B. Corolla of ray and disc florets:

*Color of bud.*—Nearest to Red-Purple Group 70A, but slightly bluer.

*Disc florets.*—Tubular, yellow in coloration, few in number, very difficult to observe, and tend to be scattered among the ray florets with a small cluster at the apex of the receptacle that is visible only when the ray florets are removed.

*General tonality.*—Venetian violet on the inside and silvery lavender on the outside.

*Color ray florets.*—Silvery lavender on the outer surfaces of the petals, between Red-Purple Group 74D and 78D, and Venetian violet on the inner surfaces, initially near Red-Purple Group 71B and often appearing darker near Red-Purple Group 71A due to the somewhat velvet appearance of the petal surface. The inner tips of the florets commonly are more blue and near Red-Purple Group 72B. As the inner surfaces of the florets mature they commonly assume a lighter coloration near Red-Purple Group 74C. The overall blossom coloration commonly is brighter during the fall. As the blossoms mature the ray florets tend to take on a more brownish coloration.

*Configuration ray petals.*—Concave in cross section, textured, and generally possess pointed tips. However, the nature of the points is variable and on the same blossom some tips commonly are denated and spurred.

C. Reproductive organs:

*Androecium.*—Generally present with disc florets and absent in ray florets.

*Gynoecium.*—Generally present with most disc florets and with most ray florets.

*Pollen.*—Formed in a slight quantity and golden-yellow in coloration.

*Fragrance.*—Typical of Chrysanthemum.

Plant

A. General appearance:

*Height.*—Short to medium, and approximately 45 to 50 cm. in height on average.

B. Foliage:

*Color (upper surface).*—Nearest to Yellow-Green Group 147A.

*Color (under surface)*—Slightly lighter green and approaches Yellow-Green Group 147B (as illustrated).

*Long day leaf count.*—Approximately 37 to 40 leaves per typical stem in a long day crop before the bud occurs.

*Configuration.*—Lobed (as illustrated), and variable with the lower lobes often being poorly defined or absent.

*Texture.*—Fleshy.

*Serration.*—Fine to coarse.

*Internode length.*—Very short.

*Stems.*—Strong, solid, angular in cross section, Yellow-Green Group 144A in coloration, and commonly with strong anthocyanin coloration at the base that is near Greyed-Purple Group 187A but somewhat lighter and commonly more blue.

*Apex.*—Mucronate.

*Base.*—Generally asymmetric.

*Claw in base of sinus between lateral lobes.*—Absent.

*Margins of sinus between lateral lobes.*—Converging but somewhat variable.

I claim:

1. A new and distinct cultivar of Chrysanthemum plant named 'Chalurido', substantially as herein shown and described, which (a) exhibits attractive large double incurved pompon blossoms that are Venetian violet on the inner ray floret surfaces and silvery lavender on the outer ray floret surfaces, (b) exhibits a flower response period of approximately nine weeks, (c) forms attractive dark green glossy foliage, (d) achieves a short to medium plant height, and (e) is particularly suited for pot mum production on a recurrent basis throughout the year.

* * * * *

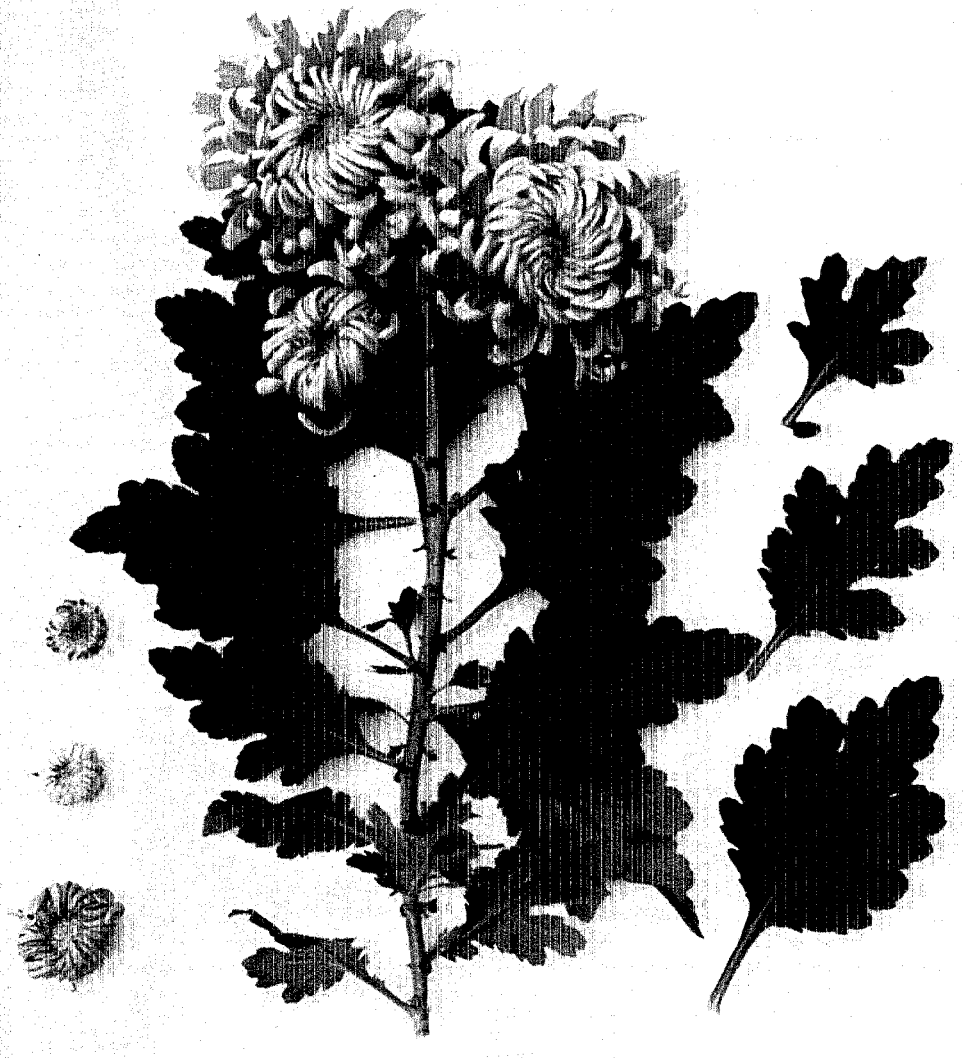
CHALURIDO 08/273.999